(12) United States Patent
Vertrees et al.

(10) Patent No.: US 11,185,622 B1
(45) Date of Patent: Nov. 30, 2021

(54) METHOD AND SYSTEM FOR CONTROLLED HYPERTHERMIA

(71) Applicant: Verthermia Acquisition, Inc., Henderson, NV (US)

(72) Inventors: Roger Vertrees, Bertram, TX (US); Jan Winetz, Incline Village, NV (US)

(*) Notice: Subject to any disclaimer, the term of this patent is extended or adjusted under 35 U.S.C. 154(b) by 0 days.

(21) Appl. No.: 17/175,676

(22) Filed: Feb. 14, 2021

(51) Int. Cl.
*A61M 1/36* (2006.01)
*A61M 1/38* (2006.01)
*A61M 1/16* (2006.01)

(52) U.S. Cl.
CPC .......... *A61M 1/369* (2013.01); *A61M 1/1629* (2014.02); *A61M 1/3627* (2013.01); *A61M 1/3666* (2013.01); *A61M 1/38* (2013.01); A61M 2205/3334 (2013.01); A61M 2205/3368 (2013.01)

(58) Field of Classification Search
CPC .............. A61M 1/1629; A61M 1/1654; A61M 1/1656; A61M 1/1696; A61M 1/267; A61M 1/3666; A61M 1/3679; A61M 1/369; A61M 2202/0423; A61M 2205/3334; A61M 2205/3606; A61M 2205/366; A61M 2230/20; A61M 2230/208; A61M 2230/50; A61M 5/1413; B01D 15/08; B01D 2215/00; B01D 2311/2626; B01D 2311/2649; B01J 20/10; B01J 20/103; B01J 20/20; B01J 20/28052; B01J 20/282; B01J 2220/58; C12Q 1/6883; C12Q 2600/156; C12Q 2600/158; C12Q 2600/172; Y02C 20/40
See application file for complete search history.

(56) References Cited

U.S. PATENT DOCUMENTS

| | | | |
|---|---|---|---|
| 6,579,496 B1* | 6/2003 | Fausset | A61M 1/369 422/44 |
| 2013/0274642 A1* | 10/2013 | Soykan | A61M 1/1613 604/5.01 |
| 2017/0246375 A1* | 8/2017 | Spearman | A61M 1/1698 |

* cited by examiner

Primary Examiner — Jennifer Wecker
(74) Attorney, Agent, or Firm — Richard L. Bigelow

(57) ABSTRACT

Methods and for treatment of cancer and other diseases including complications from late stage viral infections by inducing hyperthermia in a patient relying on withdrawing blood from the patient and returning the withdrawn blood to the patient to establish an extracorporeal flow circuit. Blood is heated by passing through the extracorporeal circuit at a controlled rate until a target body core temperature in is achieved. Usually, the blood will be subjected to a continuously re-circulating dialysis to balance electrolytes. Additionally, the blood will be subjected to a continuously recirculating regeneration through a carbon sorbent column where toxins and contaminants are removed. The blood temperature is maintained at the target blood temperature for a treatment period, and the blood is cooled after the treatment period has been completed. The method can also be effective in treating rheumatoid arthritis, scleroderma, hepatitis, sepsis, the Epstein-Barr virus, and patients with life threatening complications from other viruses, including the COVID-19 virus. A method for removing viruses from the blood supply in an external circuit is also presented.

8 Claims, 10 Drawing Sheets

467

472

METHOD AND SYSTEM FOR CONTROLLED HYPERTHERMIA

CROSS-REFERENCE TO RELATED APPLICATIONS

This divisional application claims priority from U.S. Provisional Patent Application 62/840,438 "Method and System for Controlled Hyperthermia" and from U.S. Non-Provisional patent application Ser. No. 16/846,291 Roger Vertrees "Method and System for Controlled Hyperthermia". No new matter is presented in this divisional patent application.

FEDERAL RESEARCH STATEMENT

None

FIELD OF THE INVENTION

The present invention relates generally to medical methods and devices. More particularly, the present invention relates to the extracorporeal hyperthermic treatment of a patient's blood for the treatment of cancer and other diseases and conditions, including treatment of patients with life threatening complications from viruses such as the COVID-19 virus.

BACKGROUND OF THE INVENTION

Hyperthermia has been well-accepted as a cancer treatment, particularly for solid tumors. The technique of regional perfusion and hyperthermia to treat localized malignancies in the limbs has been explored both with and without chemotherapy. Hyperthermia without accompanying chemotherapy has been successful in treating refractory malignancies. A unique and innovative method of hyperthermia to treat systemic diseases such as metastatic cancers, rheumatoid arthritis, scleroderma, hepatitis, sepsis, the Epstein-Barr virus, and patients with life threatening complications from other viruses, including the COVID-19 virus, is presented herein.

It would be desirable to provide improved methods and systems for systemic hyperthermic treatment of patients with cancer and other conditions. It would be particularly beneficial to provide such improved systems for systemic treatment to precisely raise the core body temperature to a desired target temperature by introducing a quantifiable and reproducible dose of extracorporeal heated blood while reducing and counteracting any deleterious effects on the blood and patient due to the necessary high temperature. At least some of these objectives will be met by the inventions described below.

DESCRIPTION OF THE PRIOR ART

Vertrees R A, Tao W, Pencil S D, Sites J P, Altoff D, Zwischenberger J B: Induction of whole body hyperthermia with veno-venous perfusion. ASAIO J 42:250-254, 1996;

Alpard S K, Vertrees R A, Tao W, Deyo D J, Brunston Jr, R L, Zwischenberger J B: Therapeutic hyperthermia. Perfusion 11: 425-435, 1996;

Vertrees R A, Brunston R L Jr., Tao W, Deyo D J, Zwischenberger J B. Parallel dialysis normalizes serum chemistries during veno-venous perfusion-induced hyperthermia. ASAIO J 43(5):M806-811, 1997;

Vertrees R A, Zwischenberger J B, Boor P J, Pencil S D. Oncogenic RAS Results in increased cell kill due to defective thermoprotection in lung cancer cells. Ann Thorac Surg 69:1675-80, 2000;

Vertrees R A, Bidani A, Deyo D J, Tao W, Zwischenberger J B. Veno-venous perfusion-induced systemic-hyperthermia: blood flow redistribution and thermal gradients. Ann Thorac Surg 70:644-52, 2000;

Vertrees R A, Deyo D J, Quast M, Wei G, Lightfoot K M, Boor P J, Zwischenberger, J B. Development of human to murine orthotopic xenotransplanted lung cancer model. J Invest Surg 13:1-10, 2000;

Vertrees R A, Zwischenberger J B, Woodson L, Bedell E, Deyo D J and Chernin J M. Veno-venous perfusion-induced systemic hyperthermia: case report with perfusion considerations. Perfusion 16:243-248, 2001;

Zwischenberger J B, Vertrees R A, Woodson L C, Alpard S K, Chernin J M, Bedell E A. Veno-venous perfusion-induced systemic hyperthermia percutaneous in advanced non-small cell lung cancer: initial clinical experience. Ann Thorac Surg 72:234-42, 2001;

Vertrees R A, Leeth A, Girouard M, Roach J, Kurusz, M, Zwischenberger J B. Therapeutic whole-body hyperthermia: a review of theory, design and application. Perfusion J. 17:279-290, 2002;

Zwischenberger J B, Vertrees R A, Bedell E A, McQuitty C K, Chernin J M and Woodson L C. Percutaneous veno-venous Perfusion-Induced systemic hyperthermia for lung cancer: a phase I safety study, Ann Thorac Surg; 77:1916-1925, 2004

He N, Li C, Zhang X, Sheng T, Chi S, Chen K, Wang Q, Vertrees R, Logrono R, Xie J. Regulation of lung cancer cell growth and invasiveness by Beta-TRCP. Mol Carcinog 42 (1): 18-28, 2005;

Vertrees R A, Das G C, Coscio A M, Xie J, Zwischenberger J B, Boor P J. A mechanism of hyperthermia-induced apoptosis in RAS-transformed lung cells. Mol Carcinog 44:111-121, 2005;

Vertrees R A, Das G C, Popov V L, Coscio A M, Goodwin T, Logrono R, Zwischenberger J B, Boor P D. Synergistic interaction of hyperthermia and gemcitabine in lung cancer. Cancer Biol Ther 4(10):1144-1153, 2005;

Xu Y, Choi J, Hylander B, Kraybill W G, Repasky E A. Fever-range whole body hyperthermia increases the number of perfused tumor blood vessels and therapeutic efficacy of liposomally encapsulated doxorubicin, International Journal of Hyperthermia, 2007;

Vertrees R A, Zwischenberger J B, Boor P J, Popov V, McCarthy M, Solley T N, Goodwin T. Cellular differentiation in three-dimensional lung cell cultures. Cancer Biol Ther 7(3):404-412, 2008;

Vertrees R A, McCarthy M, Solley T, Popov V, Roatin J, Pauley M, Wen X, and Goodwin T: Development of a three-dimensional model of lung cancer using cultured transformed cells. Cancer Biol Therap, 8(3): 345-356, 2009.

Suvernev A V, Ivanov G V, Efremov A V, and Tchervov R: Whole Body Hyperthermia at 43.5-44° C.: Dreams or Reality? Madame Curie Bioscience Database [Internet], 2013.

Fehr A R, Perlman S, Coronaviruses: An Overview of Their Replication and Pathogenesis, Methods Mol Biol.; 1282: 1-23. 2015.

U.S. Pat. No. 4,298,006 Systemic hyperthermia with improved temperature sensing apparatus and method U.S. Pat. No. 5,391,142 Apparatus and method for the extracorporeal treatment of the blood of a patient having a medical condition.

U.S. Pat. No. 5,476,444 Specialized perfusion protocol for whole-body hyperthermia U.S. Pat. No. 6,827,898 Hyperthermia method and apparatus. This patent presents outdated methods of providing extracorporeal heating to the patient's blood. Applicant's experience shows that the temperatures contemplated in the '898 patent are far too high and will most likely cause severe injury to the patient.

U.S. Pat. No. 9,555,184 Systems and methods for treating blood. Applicant contends that the method disclosed in this patent may be unworkable and may lead to injury to patients.

Hyperthermia in Cancer Treatment 1-800-4-CANCER Live Chat

The present invention builds upon the apparatuses, methods and analysis presented in much of the above prior art. The present invention represents a significant increase in the treatment of advanced cancers and other diseases over the apparatuses and methods disclosed in the above prior art.

SUMMARY OF THE INVENTION

The instant invention presents an improved system for treatment of several types of diseases by means of strictly controlled hyperthermia. The improved system is referred to as the Hyperthermic Treatment System (HTS). Two specific configurations of the HTS are disclosed and described herein—the Hyperthermic Extracorporeal Applied Tumor Therapy (HEATT) system which is used to treat cancer and the Hyperthermic Extracorporeal Applied Virus Therapy (HEAVT) system which is used to treat patients with life threatening complications from COVID-19 and other viral infections. In addition, further configurations of the HTS can be used to treat other maladies.

Throughout this disclosure, reference is made to specific types of equipment or apparatus such as the CardioQuip MCH-HT Modular Cooler Heater, the Medtronic Hemo-Therm Heat Exchanger and the REDY Regenerative dialysis sorbent system. These specific references to equipment and apparatuses are for ease of understanding. Similar existing or future equipment and apparatuses that exhibit similar performance characteristics may be used.

All temperatures disclosed in this application assume procedures performed at or close to sea level. Target temperatures may need to be adjusted for procedures performed at higher elevations or under other than standard temperature and pressure conditions.

In the best mode, the system is configured as shown in FIG. 1. In general, there are two primary loops in the configured Hyperthermic Treatment System (HTS): the main or primary loop and the heating loop. The main or primary loop is the treatment loop which comprises blood flowing from the patient and being heated as it passes through the heat exchanger. The main or primary loop also is comprised of at least four and preferably five pumps, the dialyzer, at least one sorbent column, and reservoirs containing intravenous (IV) fluids and electrolytes designed to ensure the blood chemistry is tightly controlled during the treatment phase. The second or heating loop is a closed loop that includes the modular cooler heater and the heat exchanger. Water or some other heat exchange medium is heated in the modular cooler heater and passes through the heat exchanger to heat the blood to the treatment regime. It is vital that the heat exchanger be of high quality such as to allow no leakage between the water and the blood. Another vital component of the HTS is the Sensor Cable Management Box. Sensor leads from the patient's body are attached to specific input portions of the Cable Management Box. The data is then presented on a monitor. The data is monitored continuously. Based on the data, temperatures and flows are adjusted during the process.

The flow in the main loop is driven by the pumps. Pump #1 is the primary pump which pumps blood at between 1.0 and 3.0 liters per minute (LPM) from the patient, through the heat exchanger and back into the patient. Prior to reaching the heat exchanger, approximately 25% of the flow from the main loop is directed by Pump #2 into the Dialysis subloop and into the Dialyzer. Pump #3 moves electrolytes from the upper and lower dialysis reservoirs into the Dialyzer. Pump #4 moves fluid from the Dialyzer through the sorbent column to remove impurities and back into one of the dialysis reservoirs. Pump #5 moves IV fluid from the IV reservoir to the heat exchanger to ensure the volume of fluid remains within range.

In a first aspect of the present invention, a method for inducing hyperthermia in a patient comprises withdrawing blood from the patient and returning the withdrawn blood to the patient to establish an extracorporeal flow circuit, typically being either veno-venous, arterio-venous or veno-arterial. The blood is flowing between a rate of 1.5 L/min to 3.0 L/min depending on patient size, heat transfer requirements, and other factors such as the patient's overall condition and type of cancer. In a further refinement of the process, blood flow may be controlled by the heat transfer rate where both temperature and blood flow rate are major factors. The blood is heated while passing through the extracorporeal circuit at a rate in the range from 0.05° C./min to 0.15° C./min (rate determined by formula) to a maximum temperature of 48° C. by circulating water through a heat exchanger at a maximum temperature of 54° C. or until a target body core temperature (weighted average of indirect cerebral, esophageal, bladder, rectal and nasopharynx) is in the range from 41.8° C. to 42.2° C. (data collected by Hall device) is achieved. The blood temperature is manipulated to maintain the target tissue temperature for a treatment period in the range from 1 hour to 3 hours, and after the treatment period has ended, the blood is cooled until the body temperature has returned to 38° C. or below. Note that longer or shorter treatment periods can be utilized depending on the patient's size, stage of cancer, etc. The inventors have found that optimum treatment is performed by rigorous adherence to dosage control as determined by the amount of HTU's delivered to the patient as defined below. In addition, the optimum temperatures and HTU's delivered will most likely be different for non-cancerous conditions such as Alzheimers or viral infections such as COVID-19. The blood flow is such that approximately 150% (+/−25% depending on treatment factors) of a patient's blood is processed through the HEATT system.

In a second aspect of the present invention, a method for inducing hyperthermia to treat a condition in a patient comprises withdrawing blood from the patient and returning the withdrawn blood to the patient to establish an extracorporeal flow circuit. The blood passing through the extracorporeal circuit is heated to raise the patient's body core temperature to a target body core temperature. The rate of heating is critically important. If the rate of heating is too slow then the cancer cells can defeat it. If it is too fast, there is risk of vascular collapse in the patient. The rate of heating is monitored in 'real-time' and displayed. The rate of heating takes into consideration individual patient size, blood flow rate and blood temperature. It is critically important to quantify the amount of heat delivered to the target tissue. We have developed, tested and verified for consistency and reproducibility a formula for determining a dose unit of heat delivered—the hyperthermia treatment unit or HTU. One HTU is defined as the amount of effective hyperthermic therapy delivered by maintaining a mean core body temperature of 41° C. for one minute. This will allow for monitoring and comparing for safety and efficacy the effect of heat on target tissue. The target body core temperature is maintained for a treatment period in the range from 1 hour to 3 hours. Once temperature drops out of therapeutic range, the HTUs are determined. After the treatment period has ended, the blood is cooled until the body temperature has returned to 38° C. or below. The blood is cooled by reducing the temperature of the water or other heat exchange medium passing through the heat exchanger. The rate of cooldown is important. If the cooldown is too fast or too slow, it could lead to adverse consequences. The data indicates that a cooldown of 30 to 60 minutes is optimal.

In a third aspect, the patient's blood is analyzed for acid-base balance and anticoagulation status by withdrawing an aliquot of blood for each assay. These elevated body temperatures will influence the acid-base balance of patients due to an increase in solubility of gases at elevated temperatures and the increased metabolic rate that results from the high temperatures. Both facts must be taken into consideration in order for patient survival and well-being. The blood is analyzed for both oxygen and carbon dioxide levels as well as pH. These values are then corrected for temperature at which they were collected by a proprietary formulae and necessary adjustments made in order to keep these values within normal accepted ranges thus avoiding a significant acidosis. Additionally, the patient's blood is analyzed for anticoagulation. Many cancer patients have abnormal clotting profiles and since the changes in temperature (hyperthermia then cooling) alters the metabolism of heparin, it is critical to monitor and amend the clotting status of these patients.

In a fourth aspect, the blood leaving the main pump (pump #1) is divided into two paths in different tubes, namely the main path and the lesser path. Blood in the main path is pumped at approximately 2.5 L/min through the heat exchanger. Blood in the lesser path is pumped at between 15% and 35% (ideally 25%) of the flow rate of blood in the main path through the dialysis circuit. The lesser blood path pumps blood into the dialyzer in which it is divided into two components: (1) formed elements suspended in sera and (2) serum with dissolved salts. The sera and formed elements, once they leave the dialyzer, re-emerge with blood at the heat exchanger. The sera/salt component is subjected to a continuously recirculating circuit that goes through a carbon sorbent column, into a dialysis holding chamber where it is re-constituted then back through the dialyzer where a transfer of salts into the patient's blood will occur. The blood is dialyzed to balance electrolytes and other serum solutes, and to introduce preselected salts selected to treat the particular condition. Dialyzing may comprise adding the preselected salts to the dialysate during treatment based on the blood analysis and/or urine output, therefore an amount added may not be realized by the patient. Verthermia's proprietary formula accurately predicts the amount of an additive that is needed. Individual electrolyte additions may be titrated in the dialysis flued and then into the blood.

In a fifth aspect of the present invention, a method for inducing hyperthermia to treat a condition in a patient comprises withdrawing blood from the patient and returning the withdrawn blood to the patient to establish an extracorporeal flow circuit. The blood passing through the extracorporeal circuit is heated to raise the patient's body core temperature to a target body core temperature. The target body core temperature is maintained for a treatment period in the range from 1 hour to 3 hours. However, the optimum delivery of cancer defeating extracorporeal heating may be more closely dependent upon the number of HTU's delivered and not necessarily the time. The blood is dialyzed with a dialysate to remove toxins and to introduce preselected salts selected to treat the particular condition. The dialysate may be maintained in a main reservoir and recycled through a dialysis circuit including a dialyzer that contacts the blood. One or more replacement reservoir(s) may be exchanged for the main reservoir after the dialysate in the main reservoir is exhausted or for any other purpose. The replacement reservoir is preferably of identical construction and may become the main reservoir. A new replacement reservoir may be further exchanged for the main reservoir after the dialysate in the replacement "main" reservoir becomes exhausted until the treatment period has ended. After the treatment period has ended, the blood is cooled until the body temperature has returned to the target rest temperature of approximately 38° C. (+/−1° C.). In an alternate embodiment, titration is controlled by proprietary Verthermia algorithms based on experiential data. Artificial intelligence based on the proprietary data algorithms controls the infusion pumps.

In a sixth aspect, the patient's blood that enters the dialyzer will be separated into serum and a portion of serum plus larger formed elements that do not dialyze. The portion without formed elements in the serum is now pumped through a sorbent column which may be composed of granular carbon, glass beads, or similar material, either loose or affixed to a matrix. In an alternate embodiment, this process will remove toxins such as tissue breakdown products as well as products of a disordered metabolism. The granular carbon is a nonselective filter and will capture many different serum components. If glass beads are used, only specific targeted molecules are removed. Once the 'cleaned-serum' exits the sorbent column it is recirculated back through the dialyzer in a continuous circuit.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

Specific embodiments of the disclosed device, delivery system, and method will now be described with reference to the drawings. Nothing in this detailed description is intended to imply that any component, feature, or step is essential to the invention.

Figure 1:
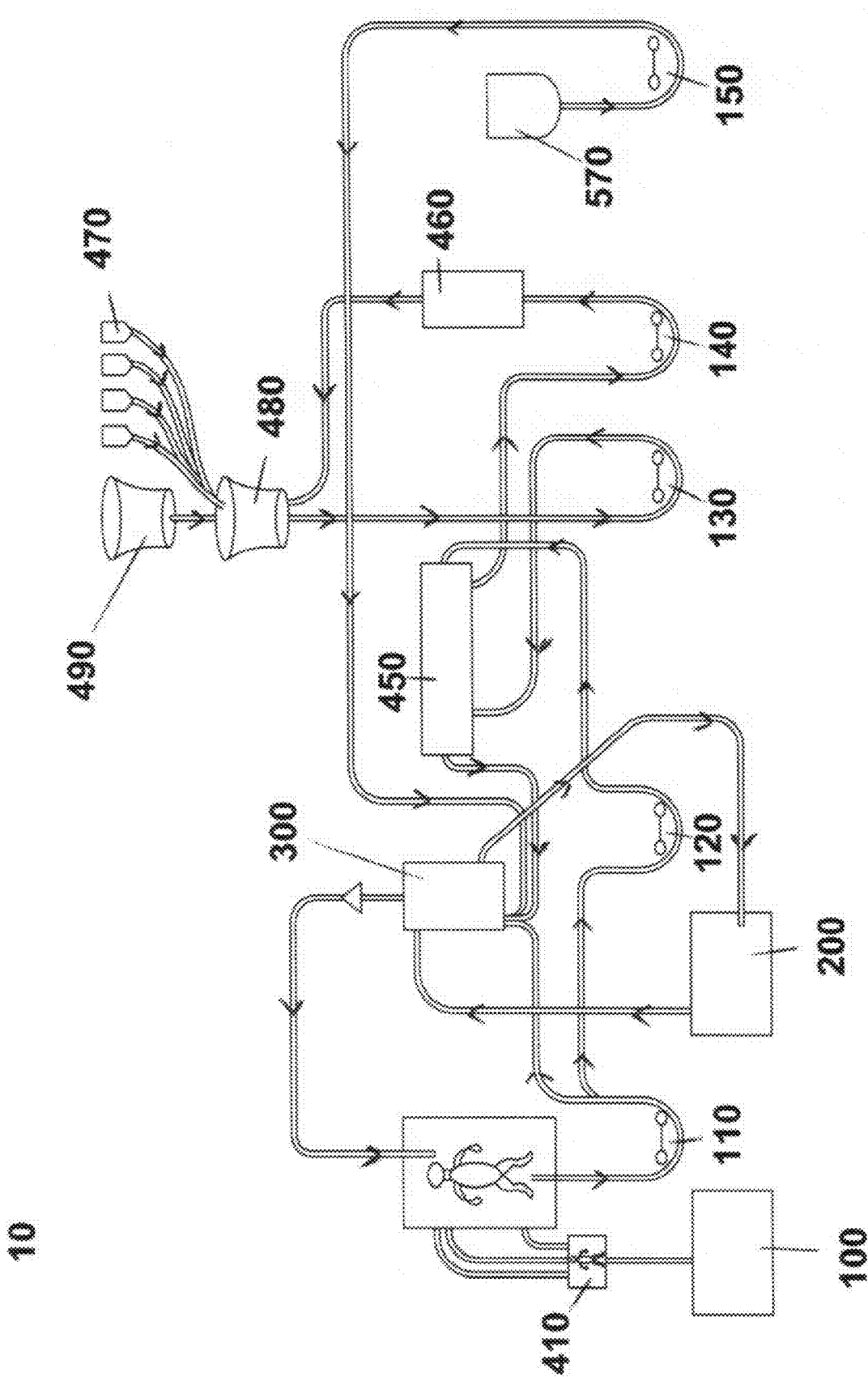
FIG. 1 is a schematic flow diagram of the Hyperthermic Treatment System (HTS) 10 showing the various major components, including the modular cooler heater 200, the monitor 400, the cable management box 410, the heart lung machine 100, the heat exchanger 300, the dialyzer 450, the dialysate reservoirs 480 and 490, the charcoal sorbent column 460 and the IV bag 550.
Figure 7:
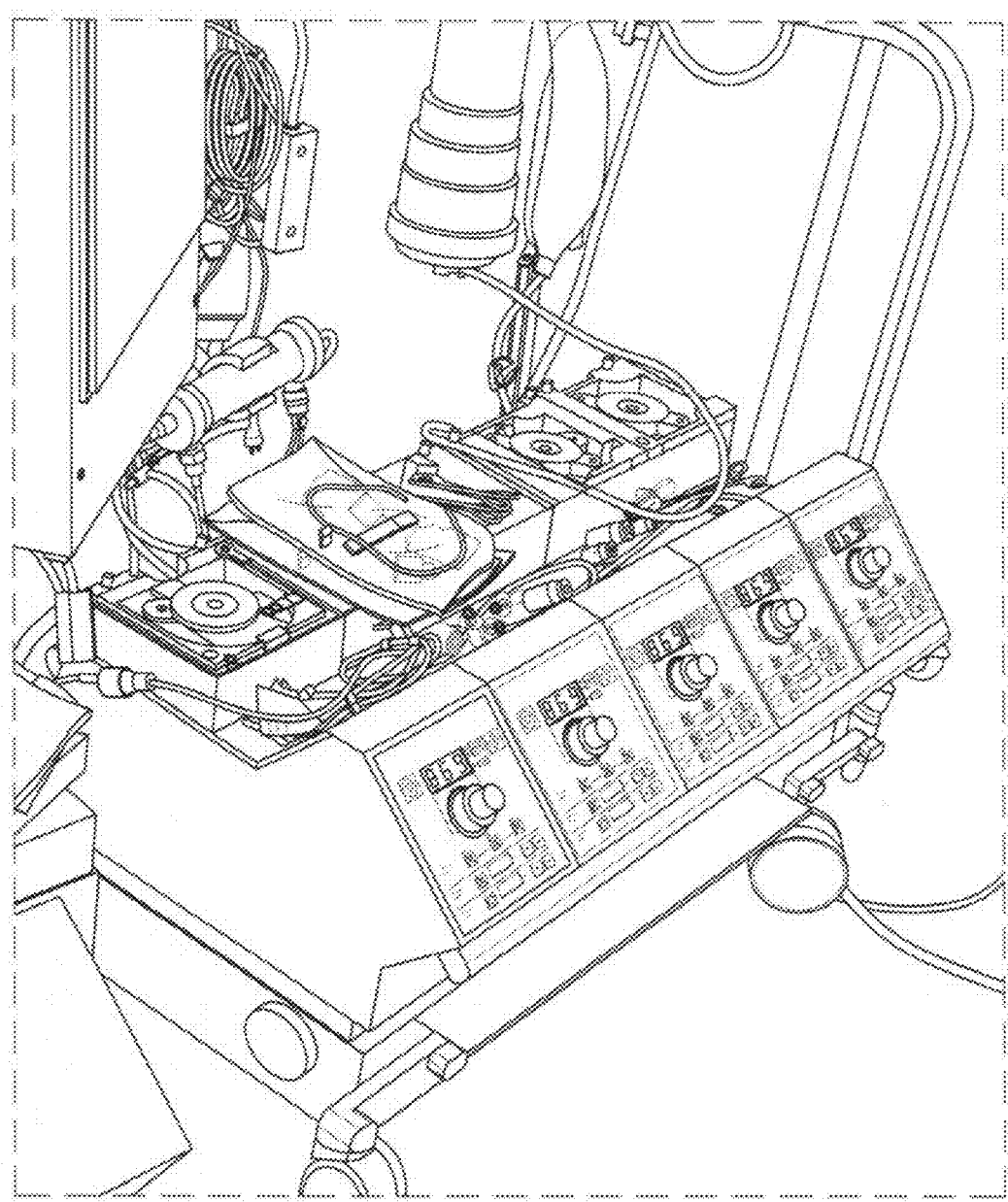
FIG. 7 shows a standard heart lung machine 100.

A flow diagram for the Hyperthermic Treatment System (HTS) 10 of the present invention is provided in FIG. 1. Non-disposable components of the HTS include a standard heart-lung machine 100 FIG. 7 having four or five pump heads. The main pump 110 on FIG. 1 moves the blood through the HTS circuit. A second pump 120 on FIG. 1 pumps blood through the dialysis circuit. A third pump 130 in FIG. 1 removes the dialysis fluid from the main dialysis reservoir and pumps it through the dialyzer 450. A fourth pump 140 in FIG. 1 draws the dialysis fluid out of the dialyzer and pumps it through the carbon sorbent column and into the bottom main dialysis reservoir. An optional fifth pump 150 in FIG. 1 is used to give additional volume into the circuit when needed.

Figure 2:
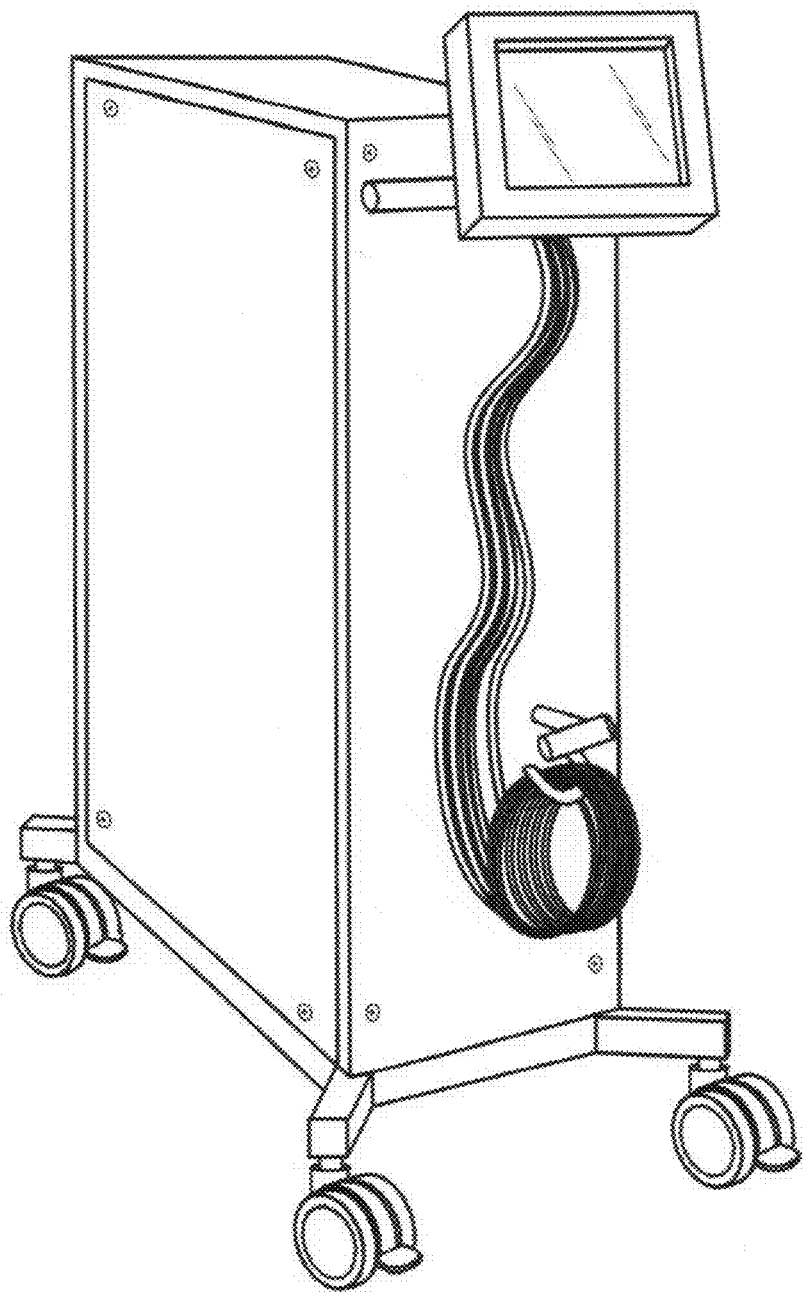
FIG. 2 is a closeup of the modular cooler heater 200.
Figure 3:
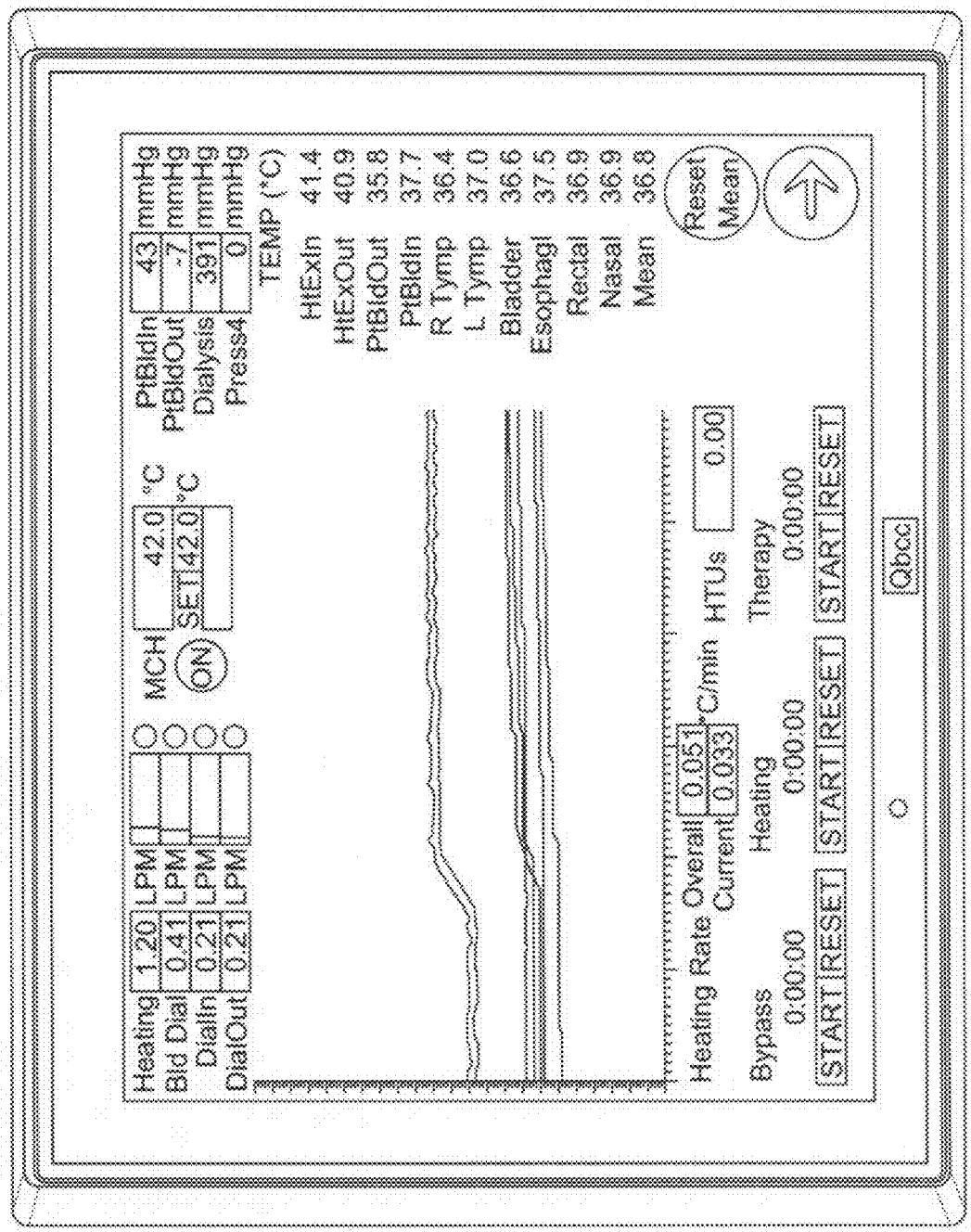
FIG. 3 is the Cardio-Quip Monitor 400.

A modular cooler heater such as a CardioQuip MCH-HT or similar device 200 in FIG. 2 is used to pump hot and/or cold water into the heat exchanger 300 in FIG. 1. The water temperature and the rate of water flow are both manually controlled by the operator. However, they could alternatively be automatically controlled in other embodiments. All the information is displayed on a CardioQuip HT-monitor or similar device 400 (FIG. 3). Displayed data include all temperatures, pressures and flows as well as the rate of heating, HTUs and all critical time values. Most of the data can be shown in graphical form allowing one to assess the time-course as well as the discrete value.

In the best mode, a perfusionist monitors and adjusts the heating and blood flow. A Nephrologist/dialysis tech monitors and adjusts levels of electrolytes.

Figure 4:
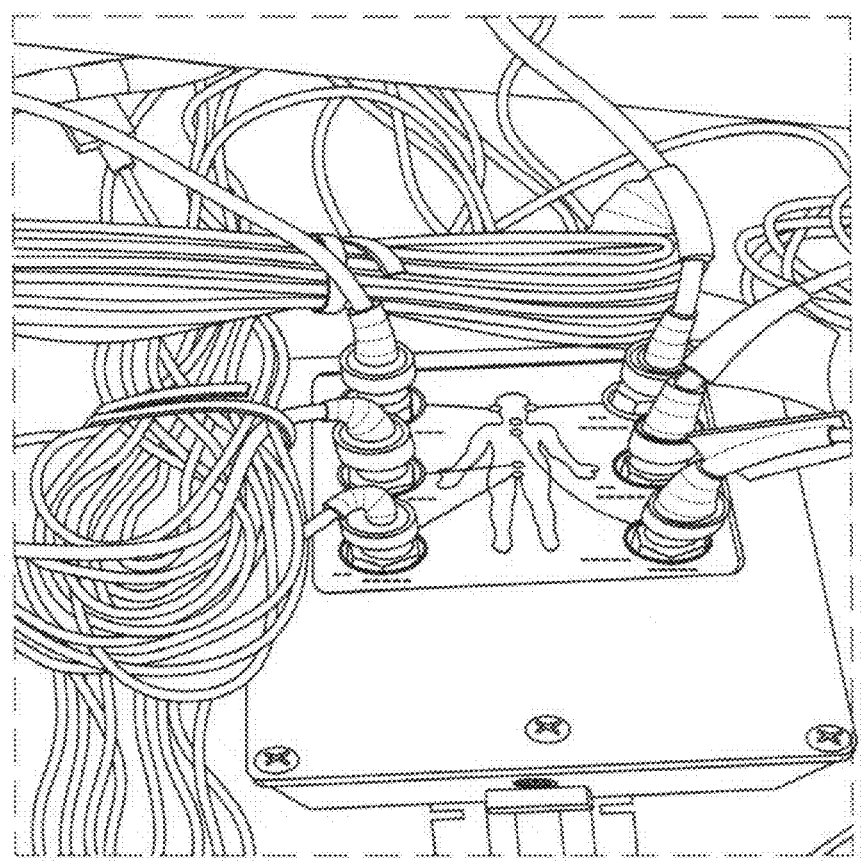
FIG. 4 is the cable management box 410.
Figure 5:
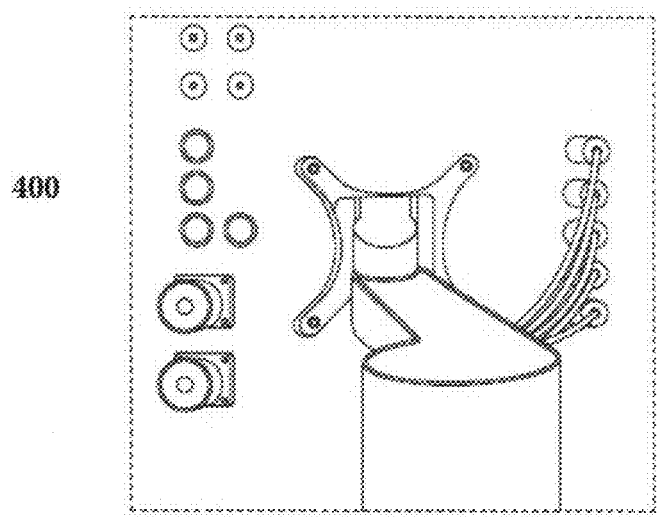
FIG. 5 shows the connections leading from the cable management box to the back of the monitor 400.

A sensor cable management box 410 (FIG. 4) is another piece of non-disposable equipment and serves as both a directory of which channel to use for what temperature and as a collection point for these many non-sterile cables. As can be seen in FIG. 4, the sensors on the patient are plugged into the illustrated anatomical locations shown on a side of the box. Therefore, the chance of connecting specific temperature or other sensors to the wrong input on the monitor/controller is significantly reduced. The sensor cable management box and all other temperature cables and pressure transducers (from the extracorporeal components of the HTS) connect to the pump controller through connections on the back of the monitor 475 (FIG. 5).

Figure 6:
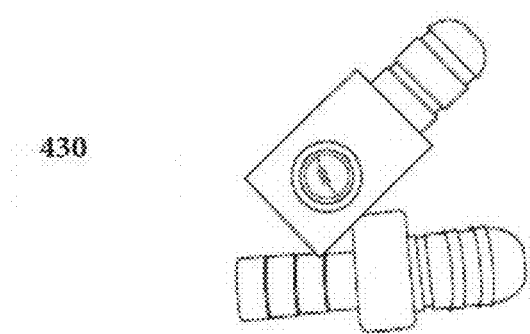
FIG. 6 is a closeup of the specially machined connectors 430.

Non-disposable stainless-steel connectors 430 that are critical to making this circuit functional are shown in FIG. 6. These connectors are specially machined to specific tolerances for the HEATT procedure. The connectors are typically made of stainless steel or similar metals or alloys due to their ability to retain heat. Suitable plastics may be determined to replace metallic connectors.

Circuit Orientation and Disposable Components

Figure 8:
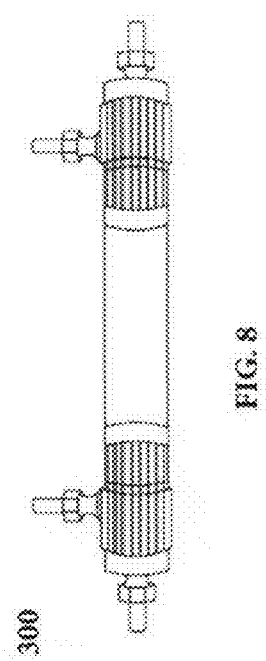
FIG. 8 is the heat exchanger 300.
Figure 9:
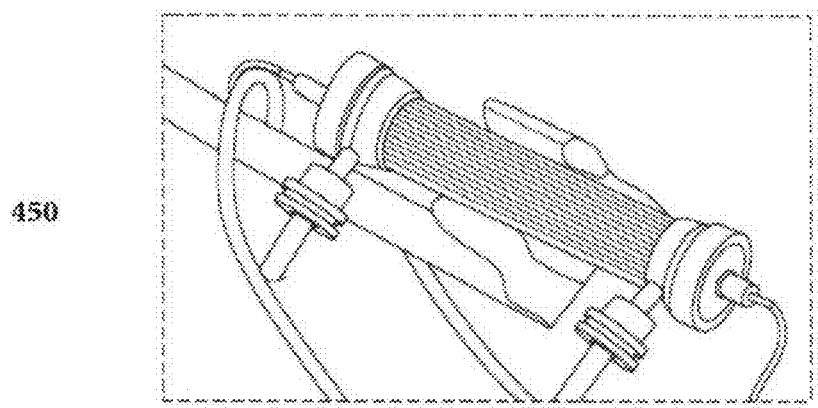
FIG. 9 is the dialyzer 450.

The extracorporeal circuit includes the HTS and is assembled in a sterile manner. Briefly, small diameter tubing, nominally ⅜-inch tubing, will be connected to a small diameter cannula, nominally a 15 Fr. cannula placed in the jugular, femoral or other suitable vein, and blood will be aspirated through the cannula by pump #1. Once through the pump, the blood divides into two separate parallel blood paths with the greater amount of the blood going directly into the heat exchanger such as a Medtronic HemoTherm Heat Exchanger or similar device 300 shown in FIG. 8 and displayed in the flow diagram FIG. 1. Main pump #1 110 flow is up to 1.5 Liters Per Minute (LPM) with about 25% diverted into the dialyzer 450. The heat exchanger 300 is connected to the MCH-HT 200 which circulates water or another heat exchange medium through the heat exchanger to control the temperature of the blood. The dialysis circuit pump (pump head #2) directs blood along the lesser blood path through the dialyzer 450 (FIG. 9) and back into the main blood stream where it then goes into the heat exchanger. Once the blood leaves the heat exchanger, the blood flows through an arterial blood filter and through small diameter tubing (nominally ¼ inch tubing) into a small diameter cannula (nominally a 13 Fr. Cannula) and into the patient's vena cava through the jugular or femoral vein.

With pump head #3 130 running about 10% slower than pump head #4 140, the dialysis fluid is aspirated from the lower dialysis holding reservoir and propelled into the dialyzer 450. Pump head #4 140 aspirates dialysis fluid from the opposite end of the dialyzer and propels it into a charcoal sorbent column 460 (FIG. 11) and into the lower dialysis main reservoir. Dialysis flow is countercurrent to blood flow through the dialyzer. Control of electrolyte salt concentrations is accomplished by altering the flow rates from the electrolyte-enhanced IV bags 470 manifolded and connected to a top of either the lower or main dialysate reservoir 480 or upper or secondary dialysate reservoir 490. A dialysis solution (bath) is located in a main (nominally the lower) dialysate reservoir 480 (FIG. 10) and dialysis enhancements in new bath solution is located in the upper or secondary reservoir. In a further refinement of the current embodiment of the instant invention, the upper reservoir is eliminated.

Recirculating Dialysis Circuit

Figure 10:
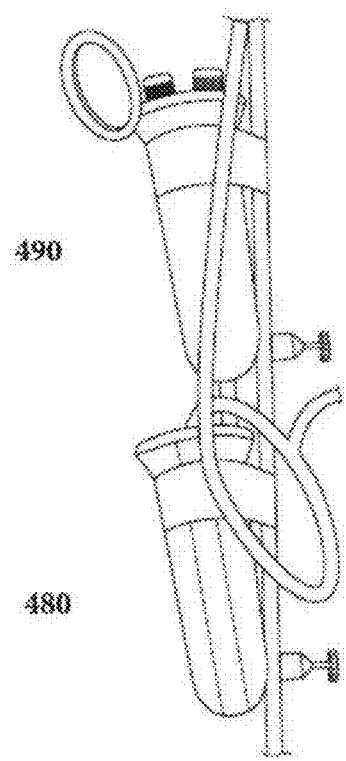
FIG. 10 shows the upper 490 and lower 480 dialysate reservoirs.
Figure 11:
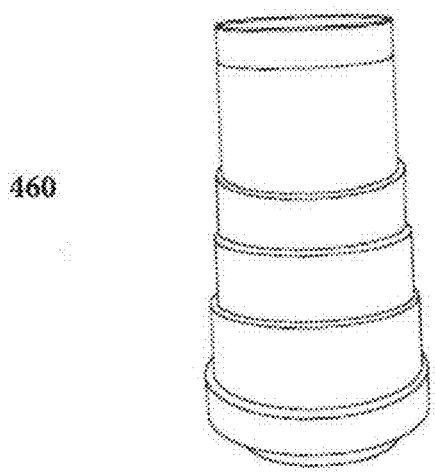
FIG. 11 is the charcoal sorbent column 460.
Figure 12:
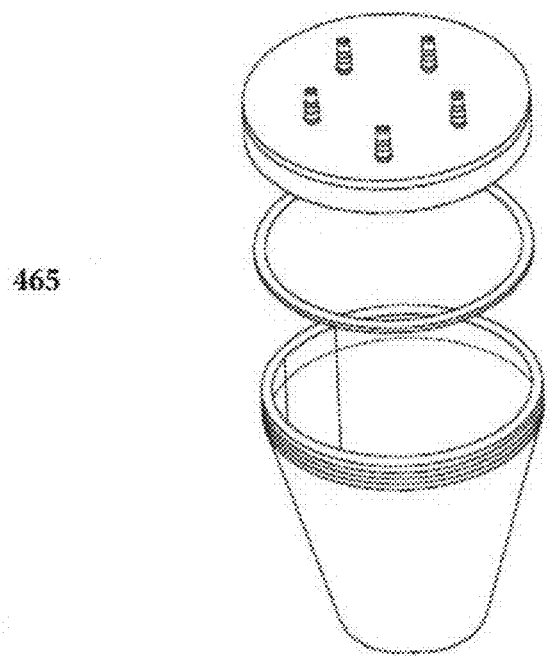
FIG. 12 is an exploded view of the dialysate reservoir 465
Figure 12A:
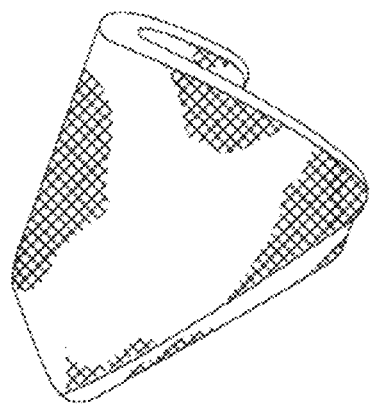
FIG. 12a is a closeup of the two stage filter 467 in each reservoir.

In the instant invention, a dialyzer 450 is used to separate and isolate a portion of the sera from formed elements in the blood (red and white blood cells, platelets and other components greater in size than approximately 50,000 daltons). The separated sera (plasma water with salts and other solutes smaller than approximately 50,000 daltons in size) is then passed through a carbon sorbent or glass bead column 460 to remove contaminants and then through the dialysis holding chamber where reconstitution of the plasma water occurs. Dialysis may be accomplished using a modified regenerative dialysis sorbent dialysis machine (such as the REDY system) or by adapting other conventional dialysis circuits to existing heart-lung pumps. In adapting a REDY sorbent recirculating dialyzer and carbon column to this application, the instant invention uses a unique dialysate reservoir 465 (FIG. 12). The reservoir has a simple design. Two reservoirs 480 and 490 are employed in each HTS circuit (FIG. 1 and FIG. 10). An upper or secondary reservoir 490 serves as a holding chamber where new dialysis is held and altered to the desired concentration of serum electrolytes. A lower or main reservoir 480 is the main reservoir which provides the dialysate necessary for continuous recirculation. Conveniently, both reservoirs may have the same design and will include multiple ports on top with a single outlet port on the bottom. A cap on top is removable to allow a quick exchange of solutions. Each reservoir has inside a two-stage filter 467 (FIG. 12a). An inner layer may be a gross filter and an outer may be a finer one. The purpose of these filters is to remove particulate contaminants that could potentially enter and damage the hollow-fiber dialyzer.

Continuous Recirculating Liver Detoxification Portion of Circuit

Figure 13:
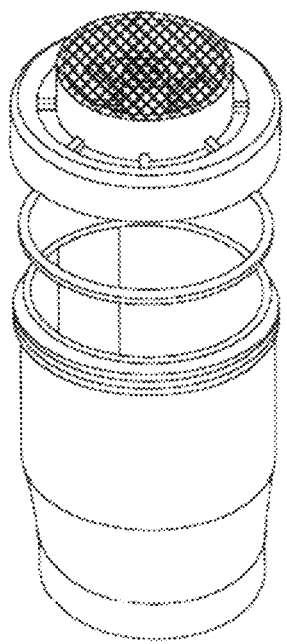
FIG. 13 shows the interior of the charcoal sorbent filter 472.

A conventional REDY charcoal sorbent filter or similar device has been modified to perform 'liver detoxification' of the recirculating dialysate for the HTS. The charcoal portion acts to detoxify the serum component of the blood. The dialysis separates blood components based on size excluding serum solutes larger than 50 kilodaltons (kDa) from passing into the recirculating bath solution. This solute/bath solution then passes through the charcoal where 'liver detoxification' occurs. A conventional REDY sorbent column may include items which are not necessary for the HTS. In particular, a conventional REDY sorbent column contains chemicals that remove anions and cations from the blood requiring the HTS to replace these ions in the recirculating bath solution. A modified charcoal sorbent filter suitable for HTS includes a main body of the filter 472 (FIG. 13) that is the container for the charcoal. A second portion attaches to the base and may contain chemicals and/or other components that will remove specific toxin(s) that can be more efficiently removed by a chemical or other component. These two portions may be removably connected by a screw connection, some bayonet type connections, or other known fastening mechanisms.

Set-Up and Priming

The HTS circuit is assembled in a sterile manner prior to the procedure. The apparatus is primed by a three-step process.

Step 1 comprises using approximately one liter of Plasmalyte A to which approximately 2,500 U heparin and approximately one ampule of sodium bicarbonate has been added is used to 'wash out' the heating portion and blood side of the dialyzer in the circuit and to displace as much air as possible. The dialysis-side of the dialyzer is prevented from priming at this point. Additionally, this prime fluid is heated to approximately 38° C.

Step 2 comprises requiring approximately two liters of heparinized Plasmalyte A to completely fill and de-air the dialysis side which includes the carbon sorbent or glass bead column. Since there is no heater in this portion of the circuit, there will be no heating in this portion of the prime. At the interface of the dialysis and heating circuits within the dialyzer, micro-air bubbles will form and be visible in the circuit. These bubbles must be eliminated at this stage which is accomplished by running both circuits simultaneously for about 30 minutes at about 38° C.

Step 3 occurs once the air has been removed and it appears the Hyperthermic Extracorporeal Applied Tumor Therapy (HEATT) perfusion will begin in about 15-minutes; the heating side prime bag is replaced with a fresh 1-liter bag of Plasmalyte-A, approximately 2500 U of heparin, approximately one ampule of sodium bicarbonate and approximately 50 mL of approximately 25% human serum albumin and allowed to recirculate through the entire circuit at approximately 38° C. perfusate temperature thus 'coating' the entire Core HFC circuit. This bag will then be removed from the prime bag connector and attached to the IV bag 550 connector for pump #5 150 and given as-needed to maintain patient-pump circulating volume.

Patient Connections

Pre-operatively in the pre-operative holding unit the patient received approximately 250 mL of a steroid that prevents the release of substances in the body that cause inflammation, such as Solu-Medrol, approximately 100 mg of thiamine, approximately 1 gram of an anti-seizure drug such as Keppra and an IV of normal saline with approximately 20 milliequivalents of KCl at approximately 200 mL per hour. In the operating room, anesthesia is induced with propofol, isoflurane, and sufentanyl. Blood is collected for baseline studies including being tested for anticoagulation properties. Patients receive a systemic dose (approximately 3 mg/Kg of body weight) of heparin (preferably beef lung heparin) prior to cannulation injected into the central line at the start of the procedure, and additional heparin or fresh frozen plasma administered whenever the Activated Clotting Time (ACT) is below 500 seconds (5 times baseline). Additionally, patients have intravenous drips of vasopressin, neosynephrine, $CaCl_2$, $MgSO_4$, $NaPO_4$, KCl, and $NaHCO_3$. After induction of anesthesia, patients are instrumented with an approximately 18-gauge radial artery catheter for monitoring arterial pressures and collection of arterial blood. A central line is placed to measure the central venous pressure and for the administration of supplemental fluids. Temperature probes were inserted into both auditory canals and connected to Ports 1 and 2 of the Sensor cable management box 410 (FIG. 4). A urinary bladder drainage catheter with integral temperature probe is inserted into the bladder and connected to a collection bag with the temperature connected to Port 4 of the Sensor cable management box 410 (FIG. 4). A rectal temperature probe is placed and connected to Port 5 of the Sensor cable management box. An approximately 13 Fr. by approximately 15 cm long Maquet cannula or similar cannula is inserted into the right internal jugular vein and advanced into the vena cava at the level of the right atrium and heparin locked. An approximately 15 Fr. by approximately 50 cm long Medtronic cannula or similar cannula is inserted into the right femoral vein, advanced into the distil vena cava and heparin locked. Another temperature probe is placed into the nasal-pharynx and connected to Port 3 of the Sensor cable management box and another temperature is inserted through the mouth and placed within the nasopharynx and connected to Port 6 of the Sensor cable management box. A sheet of aluminized Mylar® or similar material will be wrapped around the patient and tubes to minimize heat loss (optional dependent on patient temperature).

HTS Operations

Pre-mixing Phase. Upon completion of all cannula insertion, the cannula is connected to the extra-corporeal circuit and perfusion begun. The purpose of this phase is to establish, integrate and coordinate the HEATT perfusion, dialysis and the liver detoxification circuits to achieve optimal flow rates in each sector and to assure that all measured pressures and flows are within expected limits. The main blood pump flow should increase in approximately 500 mL aliquots over an approximately five minute period while observing pressures (patient and circuit) and temperatures. The three pressures measured are (1) the blood into the patient which should not exceed 300 mmHg, (2) blood out of the patient which should not be more negative than −100 mmHg and (3) the pressure drop across the charcoal sorbent or glass bead column which should be less than 400 mmHg. Additionally, circuit integrity should be assessed for water, blood or air leaks. The time spent in this phase varies from 5 to 10 minutes depending on the patient's response to perfusion. Since this is a veno-venous circuit, increasing blood flow must be done very slowly so as to not deplete $CO_2$ returning to the lungs and furthermore to not overwhelm the right side of the heart with a diluted blood volume. Optimal blood flow is patient dependent but should range about 20 to 30 mL/kg/min with a maximum flow of about 1500 mL/min.

Control of Dialysis

Blood chemistries are analyzed on an approximately 15-minute basis; the results of these analyses allow for a prompt and accurate alteration of the serum electrolytes back to normal physiological limits. Dialysis flow through pump #2 120 is started as soon after the initiation of perfusion as is possible and generally when main blood flow is about 1 liter/min. Pump #2 (dialysis pump) is adjusted to run at about 25% of the main blood pump and at this phase will be about 250 mL/min. This pump can operate with both dialysis bath in and out pumps off and their connections to the dialyzer clamped off. When these pumps are started, and the clamps removed the inflow pump to the dialyzer runs at a rate approximately 10% slower than the outflow pump; resulting in the production of an ultrafiltrate. If these pumps are operated in the reverse manner with the inflow less than the outflow, the bath solution will be delivered into the patient with the potential of "unloading" dialyzer-bound substances back into the patient. The dialysis bath solution or dialysate is a recirculating system throughout the entire procedure. The starting dialysate solution includes approximately 1 liter of normal saline to which approximately 5 milliequivalent (mEq) of potassium, approximately 40 mEq of sodium bicarbonate and approximately 4.5 mEq of calcium chloride has been added. A matching infusate continuously replenishes the dialysate bath and runs at approximately 80 cc/hr. When the bath becomes diluted by approximately 10% from the mandated ultrafiltration, the infusate is increased to approximately 100 cc/hr. At approximately 20% dilution, the bath solution is replaced with a new fresh solution and the infusate rate reduced back to approximately 80 cc/hr.

Should the blood chemistry analysis indicate that the patient has a low serum potassium level (approximately 10% drop in value), then the dialysate is changed from 4 to 6 mEq: an additional drop of approximately 10% in the serum potassium causes the start of an additional infusate of approximately 100 mEq KCL/250 cc D5W (5% Dextrose in water) given through a central vein at approximately 50 cc/hr. If the potassium is still outside the normal range, the dialysate bath is increased by approximately 1 mEq and the infusate is increased by approximately 25 cc/hr.

Should the blood chemistry analysis show a low calcium level (decrease of approximately 10%), then a central drip infusate of approximately 8-grams of CaCl in approximately 500 cc D5W at approximately 100 cc/hr is started. For every approximately 5% drop in the serum calcium level below target range, there is an increase in the infusate rate by approximately 50% more than the previous rate. If the calcium level is too high, the dialysate bath is changed to an approximately 3-mEq bath from the prior approximately 4-mEq bath and the infusate is decreased to approximately 50 cc/hr.

Should the blood chemistry analysis show a low pH (acidosis), an infusate, composed of approximately 400 mEq NaHCO3/LDSW, is started at a rate of approximately 100 cc./hr. For every approximately 5% drop in pH from the target level, the infusate rate is increased by approximately 50 cc./hr. If the correction of the pH is not reached with the above change in the infusate rate, then the rate is increased by approximately 100 cc/hr from the baseline rate.

Should the blood chemistry analysis show a low serum phosphorus, an infusate of NaHPO4 approximately 90 mMOL/LDSW is started at approximately 100 cc/hr. For a serum phosphorus level less than 3.5-mg/100 cc, the infusate rate is increased by approximately 25% from the previous rate. If the serum phosphorus is still not normalized, the infusate rate is increased by approximately 50% from the previous rate. For a serum phosphorus greater than 5 mg/100 cc, the infusate rate is decreased by approximately 25% from the previous rate. If the serum phosphorus is still elevated, then the infusate rate is further decrease by approximately 50% from the previous rate.

Control of Liver Detoxification

Control of liver detoxification is accomplished in the sorbent column and is a function of mass transfer. The more of the dialysis solution that is exposed to the charcoal or glass beads, the more toxin is removed. Therefore, this is flow dependent. To remove more toxins, the flow through the carbon needs to be increased. The limiting factor here is the pressure drop across the charcoal or glass bead sorbent column which should not exceed 400 mmHg.

Mixing Phase

Blood samples are obtained at least every 15 minutes during the procedure, or when otherwise clinically indicated. Temperatures will be monitored and recorded at the following sites: deep esophagus, right and left tympanic membranes, rectum, bladder, and nasopharynx. The average core temperature (Tc) is defined as the mean value of the esophagus, right and left auditory canals, rectum, nasal-pharyngeal, and bladder temperatures. The patient will be allowed to stabilize for approximately 15 minutes on veno-venous bypass at approximately 38° C. prior to starting the heating phase. This also allows establishing a hemodynamic and metabolic baseline for that individual. Once main blood flow has been established, the dialysis pump (#2) will be adjusted to divert approximately 25% of the blood into the dialysis circuit. Both dialysis bath pumps should not exceed approximately 50% of pump #2 flow. The purpose of this phase is to equilibrate the patient's temperature to the circuit temperature before starting to heat as this will give us clearer baseline chemistry values. After the 15-minute interval is completed, the heating phase begins.

Heating Phase

The specialized CardioQuip Heater Cooler or similar device will be engaged to heat the blood to reach therapeutic hyperthermia interval (T6=42° C.). A water-to-blood temperature gradient will be maintained below approximately 10° C. The device has been customized to not exceed a maximum water bath temperature of 52° C. (and a maximum blood temperature of 48° C.). A proprietary formula has been developed that is called "the heating rate" which calculates heat transfer and then makes a prediction going forward. If the prediction falls outside the limits, then an alarm will indicate that heating is either too fast or too slow. Currently, our standard is set at 0.1° C./minute±1.2 SD. As the average core temperature approaches approximately 42° C., attention must be directed to the auditory canal temperatures as these temperatures should not exceed 42.2° C. As the average core temperature exceeds 40.8° C., another formula called hyperthermic therapy units (HTUs) is called into play. This formula calculates the amount of heat that the body is receiving in real-time and is equivalent to a 'dose of heat.' Once the average core temperature reaches 42° C., water bath temperature will be reduced in stages such that the target temperature of approximately 42° C. is maintained. When water-bath temperature is in the range of 44° C., a reduction in blood flow will help to reduce the amount of heat delivered to the patient. The final set of mathematical relationships employed is for the temperature correction of the blood gases and pH. Blood gas analyzers measure oxygen, carbon dioxide and pH at approximately 37° C. regardless of the temperature at which the blood was collected. Since the solubility of gases in solution is dependent upon the temperature of the solution, this results in the need to derive the 'true' value for these variables. These calculations are applied to both arterial (collected at the radial artery) and venous blood (blood out of patient to pump) gas results once hyperthermia is initiated until the body core temperature returns to normal. Although there are many different forms of these equations, we have found that the following relationships work well. With increasing temperature, more $CO_2$ is retained by the blood resulting in a respiratory acidosis. The partial pressure of $CO_2$ ($pCO_2$) of the patient at the elevated temperature can be found by adding approximately 2-mmHg for each degree above 37° C. to the $pCO_2$ measured by the machine. The partial pressure of $O_2$ ($pO_2$) of the patient at the elevated temperature can be found by adding approximately 5 mm Hg for each degree above 37° C., and the pH can be found by subtracting approximately 0.015 pH units for each ° C. above 37° C.

Therapeutic Phase

This phase starts once the target temperature of 42.0±0.2° C. has been reached as determined by the average core calculations and it will be maintained for approximately 120 minutes. Not all temperatures will be at 42° C. at the start of the therapeutic interval and some may never reach 42° C. at all. This is often more of a problem with the temperature probe than with the site not getting hot enough.

Pump Orientation

The following information must be displayed and monitored on a continuous basis as is shown above:

(1) flow rate in LPM for all three pumps, for example, 0.78 for the main (i.e. Pump #1), 0.34 for the dialysis pump (pump #2), and 0.20 and 0.19 for the dialysis bath pumps (pumps #3 and #4).

(2) MCH data of 45° C. with a water set point of 45.1° C.

(3) System pressures in the upper right corner showing a patient inflow pressure of 27, outflow of 0 and a dialysis sorbent pressure of 375 mmHg.

(4) On the right side of the monitor are the various temperature readings starting with heat exchanger in water temperature (HtExIn), heat exchanger water out, patient blood temperature out (PtBldOut), patient blood in temperature, then all the body temperatures. The mean is calculated continuously.

(5) Across the bottom are three clocks showing total pump time, heating time and therapy time.

(6) Immediately above the clocks is the output from the heating rate formulae expressed as overall and current, and the HTUs (128.30).

(7) In the center of the screen is a graphic representation of the time-course for each measured temperature. This is particularly useful during the heat up and cool down phases. If the main pump flow has been decreased during this period, starting at about 110 minutes return the flow to the optimal for that patient which should be about 1500 mL/min. This higher flow rate will be needed in order to effectively cool the patient however too high a flow rate encourages veno-venous shunting resulting in insufficient cooling. This information and data is continuously monitored by the Perfusionist.

Cooling, De-Cannulation and Discontinuation of HEATT Procedure.

After approximately 120 minutes at the target temperature or alternatively when the prescribed number of HTU's is administered, the water set temperature is reduced to approximately 38° C. The gradient between the patient blood out temperature and the heat exchanger water in temperature must be carefully observed and monitored as this gradient is critical. Once this gradient is gone, the water set temperature is reduced to approximately 35° C. Perfusion can be discontinued once the average core temperature and patient blood outlet temperatures are stable at approximately 38° C. Once the perfusion is complete, the residual volume in the perfusion circuit will be returned to the patient. Next, cannulae will be removed, heparin will be reversed with protamine and cannulation sites closed and verified that no bleeding is occurring. ACT should be about 120±20 seconds and a heparin: protamine titration can be done to verify that all the heparin has been neutralized.

Aside from the patient's maximum core body temperature, the most critical component of a hyperthermic procedure is the rate of increase in core body temperature. For patient safety, therefore, the heating rate must be monitored closely. Previous studies have shown that thermoresistance can be manifest within about 200 minutes. Therefore, one needs to be at the therapeutic temperature by this time. (Henle, K J and Roti Roti, J L, Radiat Res 82, 138-145, 1980). A core body temperature increase of 0.25° C./min may be fatal, whereas heating at half that rate, or ~0.12° C./min, is safe.

The HEATT device uses the patient's mean core body temperature to calculate the overall rate of heating, which is found by subtracting the initial temperature To from the current temperature $T_i$ and dividing by the total elapsed time in minutes. The device also calculates the current rate of heating, which is found by subtracting the temperature three minutes in the past Ti−3 from the current temperature Ti and dividing the result by 3. A heating rate more than 0.12° C./min triggers an alarm. Other pre-alarm setpoints may be instituted to warn the Perfusionist that the heating rate alarm limit is approaching.

Overall and Current Heat Rate $T_o$=Patient's initial temperature.
$T_i$=Patient's current temperature
$T_{i-3}$=Patient's temperature three minutes earlier.
$t_{tot}$=Total elapsed heating time
OHR=Overall Heat Rate
CHR=Current Heat Rate $$OHR = \left(\frac{T_i - T_o}{t_{tot}}\right)$$

$$CHR = \left(\frac{T_i - T_{i-3}}{3}\right)$$

One of the unresolved challenges in hyperthermic treatment is the ability to quantify a particular "dosage" of hyperthermia. Measuring the actual amount of energy added to the patient is not helpful because variances in patient physiology and environmental conditions have a significant impact on the energy required to deliver effective hyperthermic treatment. Ultimately, though, the only critical measurement is the actual core body temperature. If the core temperature is correct, therapy occurs. Other factors are essentially irrelevant. Therefore, a new unit has been developed: the HTU, or Hyperthermic Treatment Unit. One HTU is defined as the amount of effective hyperthermic therapy delivered by maintaining a mean core body temperature of 41° C. for one minute.

Because effective therapy begins at a minimum temperature ($T_{min}$), calculations of HTU delivery are only valid when the instantaneous temperature $T_i$ is at or above $T_{min}$. $T_{min}$ is dependent upon the particular disease being treated.

Based on the therapy effect vs. temperature curves (Vertrees R A, Brunston R L Jr., Tao W, Deyo D J, Zwischenberger J B), parallel dialysis normalizes serum chemistries during veno-venous perfusion-induced hyperthermia. ASAIO J 43(5):M806-811, 1997), the effective therapy increases in an approximately 2× linear fashion between 41-43°, with therapy delivered at 43° C. being three times as effective as at 41° C. The hyperthermic therapy H being delivered during time interval i is thus calculated as:

$$T_i \geq T_{min}$$

Where:
1. $t_i$ and $t_{i-1}$ are times in minutes.
2. $T_i$ and $T_{min}$ are temperatures in ° C.
3. $H_i$ is the number of HTU's delivered in a given incremental time interval.
4. $H_T$ is the total number of HTU's delivered to the patient during the treatment period.

$$H_i = \left(1 + (T_i - 41)\left(\frac{t_i - t_{i-1}}{60}\right)\right)$$

For example, the number of HTUs delivered in a three second time interval during which the mean core temperature is 41.5° C. is calculated as:

$$H_i = \left(1 + (41.5 - 41)\left(\frac{3}{60}\right)\right) = 0.075$$

The total number of HTU's delivered to the patient is the sum of the incremental values.

$$H_T = \sum_{i=1}^{n} H_i$$

Treatment of Late Stage COVID-19 Virus Infection

A modification of the HEATT method (Hyperthermic Extracorporeal Applied Virus Therapy [HEAVT]) has been shown to be effective for treating patients with life threatening complications from COVID-19 and other viral infections. In general, the treatment for late stage COVID-19 patients is similar to treatment of cancer patients with the notable exceptions of (1) limiting the upper range of temperature to approximately 40° C. and (2) modifying the procedure to include an oxygenator, given the fact that most patients would be in respiratory failure. Treatment is performed for approximately two hours or until a suitable amount of HTU's is applied to the patient.

The two hour duration at or about at the upper range temperature exposes approximately 150% of the patient's blood volume to both the heat and hemodiaultrafiltration. Understanding that these patients are in respiratory failure, an oxygenator can be introduced into this circuit thus oxygenating and removing carbon dioxide. Veno-venous perfusion with an oxygenator is a commonly used perfusion technique to support patients in respiratory failure which is referred to as the Extracorporeal Membrane Oxygenation (ECMO) process. After the approximately two hours of heating, the patient will be returned to a normothermic state and will continue to be supported with veno-venous ECMO until the patient can be weaned from it as determined by their respiratory status. The hemodiaultrafiltration will be switched over to continuous veno-venous hemofiltration (CVVH) thus allowing for removal of residual proinflammatory acute-phase cytokines.

CVVH (Continuous Veno-Venus Hemofiltration) is a process where a dialysis catheter is placed in one of the main veins of the body. This catheter has two separate lines. Blood flows out of the catheter and into the CVVH machine, which then goes into a filter where waste fluid is taken off. Fluids and electrolytes (i.e. sodium and potassium) are then replaced. Finally, the blood is returned back to the patient through the catheter. In addition, large molecules are removed including, but not limited to, pro-inflammatory cytokines. This can have positive clinical impact where the inflammatory process plays a strong clinical role. For example: In the article "Immunomodulatory Effect of Continuous Venovenus Hemofiltration during Sepsis", (Giuseppe Servillo, Maria Vargas, Antonio Pastore, Alfredo Procino, Michele Iannuzzi, Alfredo Capuano, Andrea Memoli, Eleonora Riccio, and Bruno Memoli Biomed Res Int. 2013; 2013: 108951. Published online 2013 Jul. 23. doi: 10.1155/2013/108951) it was shown that CVVH removes the pro-inflammatory cytokine mediator Il-6 with positive clinical results. This was also confirmed in several recent articles. In an article published in the Journal Frontiers Immunol. January 2019 "On the Effects of Changes in the Level of Damage Associated Molecular Patterns Following CVVH Therapy on Outcomes on Acute Injury Patients with Sepsis", it was shown that there was a significant reduction in the levels of circulating Il-6, TNF, and DAMP (damage associated molecular patterns such as: Mitochodrial DNA, Nuclear DNA, and Heat Shock Proteins), also with positive clinical results. This is just an example of two of many articles published stating that CVVH may have a positive impact on diseases by employing pro-inflammatory cytokine reduction.

Upon discontinuation of this procedure, an upregulation of the immune system in cancer patients has been shown and is expected to occur in the chronic phase of COVID-19 also as the immune system begins to recognize the presence of the foreign glycoproteins.

In another alternate embodiment of the present invention, blood from the blood supply can be heated in an external circuit to eliminate viruses, including the COVID-19 virus. Implementing such a method can ensure that blood that was donated by a person who was infected with a virus, but who was asymptomatic when the blood was donated, can be cleansed of a virus. Normally red cells are stored for up to six weeks (forty-two days) before they are disposed of. If present, the virus would most likely reside in the red cells. This would present ample opportunity for an infected, yet asymptomatic, person to donate blood and eventually have that infected blood infect another person during surgery. This embodiment of the instant invention presents a methodology for avoiding the same type of spread of viruses through surgery, transfusions, etc. that occurred during the AIDS epidemic.

Whereas the best mode for the present invention involves establishing an extracorporeal circuit that necessarily included the patient, in this alternate embodiment, blood from the blood supply that may have been infected is introduced into a stand-alone circuit. The blood should be slowly heated in a dynamic circuit from its normal storage temperature of about 6° C. to a treatment range of 40° C. to 49° C. and preferably 45° C. to 47° C. for a period of 10 to 40 minutes and preferably 15 to 30 minutes. All normal precautions exercised during treatment and handling of blood should be exercised in order to ensure that the blood is not damaged. Following treatment, the blood should be cooled to room temperature and then stored at the normal storage temperature of about 6° C.

The blood is heated and cooled using a modular cooler heater (MCH) or similar device. Blood chemistry is monitored throughout to ensure the blood is not damaged and to further ensure that blood chemistry remains with acceptable levels.

What is claimed is:

1. A method for inducing hyperthermia to treat a condition in a patient, said method comprising:
    a. withdrawing blood from the patient and returning the withdrawn blood to the patient to establish an extracorporeal flow circuit;
    b. heating blood passing through the extracorporeal circuit to raise the patient's body core temperature to a target body core temperature;
    c. controlling the rate of heating and blood flow to within defined limits;
    d. maintaining the target body core temperature for a treatment period in the range from 1 hour to 3 hours;
    e. analyzing blood for both oxygen and carbon dioxide levels, as well as pH, and correcting the above levels for temperature;
    f. dialyzing the blood in a dialyzer and dialysis circuit to introduce preselected salts selected to treat the metabolic condition;
    g. moving the blood throughout the extracorporeal flow circuit by means of up to five pumps connected to a heart lung machine, wherein the five pumps further comprise a main pump (#1), a dialysis pump (#2), two dialysis bath pumps (#3 and #4), and an optional IV fluids pump (#5);
    h. detoxifying the blood by continuously passing it through a charcoal or glass bead sorbent column; and
    i. after the treatment period has ended, cooling the blood until the body temperature has returned to 38° C. or below.

2. A method as in claim 1 where the blood from pump #1 is split into two paths, wherein one path continues into the heat exchanger and the second path travels through the dialysis circuit.

3. A method as in claim 1 where the blood from pump #1 is split into two paths, wherein one path continues into the heat exchanger and the second path travels through the dialysis circuit at between 15% and 35% of the flow rate of the first path.

4. A method as in claim 1 where the blood that enters the dialyzer is separated into serum and a portion of serum plus larger formed elements that do not dialyze.

5. A method as in claim 1 where pump #3 operates approximately 10% slower than pump #4.

6. A method as in claim 1 where dialysis fluid is aspirated from a lower dialysis holding reservoir and propelled into the dialyzer.

7. A method as in claim 1 where pump #4 aspirates dialysis fluid from the dialyzer and propels it into the sorbent column and then into a lower dialysis holding reservoir.

8. A method as in claim 1 where control of electrolyte salt concentrations is accomplished by altering the flow rates from a series of electrolyte-enhanced IV bags manifolded and connected to a top of either a lower dialysate reservoir or an upper dialysate reservoir.

* * * * *